United States Patent [19]

Dubroeucq et al.

[11] Patent Number: 5,017,576

[45] Date of Patent: * May 21, 1991

[54] QUINOLYLOXYACETAMIDES

[75] Inventors: Marie-Christine Dubroeucq, Enghien Les Bains; Jean-Marc Paris, Vaires Sur Marne; Christian Renault, Taverny, all of France

[73] Assignee: Rhone-Poulenc Sante, Antony, France

[*] Notice: The portion of the term of this patent subsequent to Mar. 1, 2005 has been disclaimed.

[21] Appl. No.: 405,294

[22] Filed: Sep. 11, 1989

[30] Foreign Application Priority Data

Sep. 13, 1988 [FR] France .................. 88 11903

[51] Int. Cl.$^5$ .............. C07D 215/233; C07D 413/12; C07D 417/12
[52] U.S. Cl. ................ 514/228.2; 514/235.2; 514/312; 544/62; 544/128; 546/153
[58] Field of Search ............. 544/62, 128; 546/153; 514/228.2, 235.2, 312

[56] References Cited

U.S. PATENT DOCUMENTS 4,728,647  3/1988  Benavides et al. ............ 514/222
4,788,199 11/1988  Benavides ................... 514/259
4,788,204 11/1988  Benavides et al. ............ 514/311

FOREIGN PATENT DOCUMENTS 0205375 12/1986 European Pat. Off.
0210084  1/1987 European Pat. Off.

Primary Examiner—Mukund J. Shah
Assistant Examiner—Philip I. Datlow
Attorney, Agent, or Firm—Morgan & Finnegan

[57] ABSTRACT

Quinoline derivatives of formula:

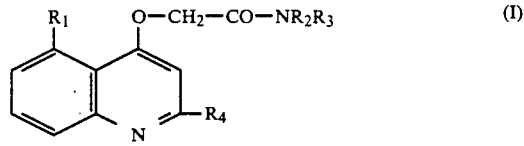

in which
either $R_1$ denotes trifluoromethyl, $R_2$ and $R_3$ form, together with the nitrogen atom to which they are attached, morpholino and $R_4$ denotes a 4-methylphenyl, 4-chlorophenyl, 2-, 3- or 4-fluorophenyl, 4-methoxyphenyl, 4-methyl-3-fluorophenyl, 2,4-difluorophenyl or 4-aminophenyl, or $R_1$ denotes trifluoromethyl, $R_2$ and $R_3$ form, together with the nitrogen atom to which they are attached, thiomorpholino, or $R_2$ denotes methyl and $R_3$ denotes 2-methoxyethyl and $R_4$ denotes 4-methylphenyl, or $R_1$ denotes chlorine fluorine, or methoxy, $R_2$ and $R_3$ form, together with the nitrogen atom to which they are attached, morpholino, and $R_4$ denotes 4-methylphenyl, are useful as anxiolytics, hypnotics, anticonvulsants and antiepileptics.

7 Claims, No Drawings

QUINOLYLOXYACETAMIDES

DETAILED DESCRIPTION OF THE INVENTION

The present invention provides, as novel compounds, the quinoline derivatives of formula:

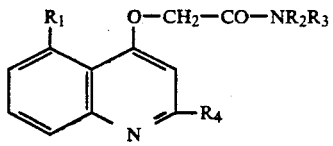

in which
either $R_1$ denotes trifluoromethyl, $R_2$ and $R_3$ forms, together with the nitrogen atom to which they are attached, morpholino and $R_4$ denotes 4-methylphenyl, 4-chlorophenyl, 2-, 3- or 4-fluorophenyl, 4-methoxyphenyl, 4-methyl-3-fluorophenyl, 2,4-difluorophenyl or 4-aminophenyl, or $R_1$ denotes trifluoromethyl, $R_2$ and $R_3$ form, together with the nitrogen atom to which they are attached, thiomorpholino, or $R_2$ denotes methyl and $R_3$ denotes 2-methoxyethyl, and $R_4$ denotes 4-methylphenyl, or $R_1$ denotes chlorine or fluorine or a methoxy radical, $R_2$ and $R_3$ form, together with the nitrogen atom to which they are attached, morpholino and $R_4$ denotes a 4-methylphenyl radical.

The compounds of formula (I), with the exception of that for which $R_4$ denotes a 4-aminophenyl radical, may be prepared by reacting a quinolone of formula:

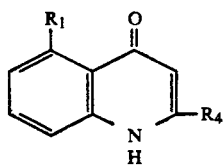

in which $R_1$ and $R_4$ have the same meanings as in the formula (I), except that $R_4$ cannot denote 4-aminophenyl, with a compound of formula:

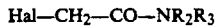

in which $R_1$ and $R_4$ have the same meanings as in the formula (I), except that $R_4$ cannot denote 4-aminophenyl, with a compound of formula:

in which $R_2$ and $R_3$ have the same meanings as in the formula (I) and Hal denotes halogen, (preferably chlorine or bromine).

This reaction is preferably performed in the presence of an alkali metal carbonate such as sodium or potassium carbonate, in an organic solvent such as a ketone, e.g. 2-butanone, at a temperature between 20° C. an the boiling point of the solvent.

The quinolones of formula (II) may be obtained by the cyclization of a derivative of formula:

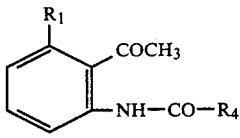

in which $R_1$ and $R_4$ have the same meanings as in the formula (II).

This cyclization is generally performed in an organic solvent such as benzene, toluene or xylene, in the presence of sodium tert-butylate, at the boiling point of the solvent.

The compounds of formula (IV) may be obtained by the action of an amino derivative of formula:

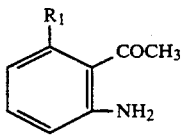

in which $R_1$ has the same meanings as in the formula (I), or a salt of such a derivative with an acid, on a chlorinated derivative of formula:

in which $R_4$ has the same meanings as in the formula (II).

This reaction is preferably performed in an organic solvent such as benzene, toluene or xylene, in the presence of pyridine, at a temperature in the region of 20° C.

The amino derivatives of formula (V) may be obtained by the oxidation of a compound of formula:

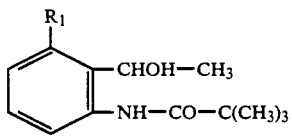

in which $R_1$ has the same meanings as in the formula(I), followed by liberation of the amine group.

The oxidation may be accomplished by means of chromic anhydride in a ketone such as acetone at a temperature of between $-5°$ C. and 0° C., and the liberation of the amine with an acid such as hydrochloric acid in an alcohol such as methanol or butanol.

The derivatives of formula (VII) may be prepared by the action of acetaldehyde on a derivative of formula:

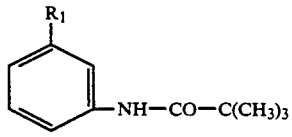

in which $R_1$ has the same meanings as in the formula (I).

This reaction is accomplished by means of butyllithium in an organic solvent such as hexane at a temperature of between $-78°$ C. and 20° C.

The derivatives of formula (VIII) may be obtained by the action of pivaloyl chloride on a derivative of formula:

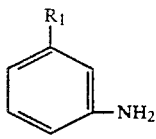

(IX)

in which $R_1$ has the same meanings as in the formula (I).

This reaction is preferably performed in an organic solvent such as benzene or toluene, in the presence of a trialkylamine or of pyridine, at a temperature of between 0° C. and 20° C.

The derivatives of formula (II) for which $R_1$ denotes chlorine or fluorine may also be obtained by the action of a derivative of formula (IX), in which $R_1$ has the same meanings as above, on ethyl 4-methylbenzoylacetate.

This reaction is generally accomplished using polyphosphoric acid at a temperature of between 100° and 170° C. The product is obtained mixed with 7-fluoro- or 7-chloro-2-(4-methylphenyl)-4-quinolone. This mixture may be used without further purification for the preparation of the compound of formula (I).

The compounds of formula (I), with the exception of that for which $R_4$ denotes a 4-aminophenyl radical, may also be prepared by the action of an acid chloride of formula:

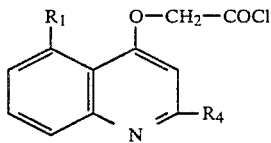

(X)

in which $R_1$ and $R_4$ have the same meanings as in the formula (I), except that $R_4$ cannot denote a 4-aminophenyl radical, on an amine of formula:

HNR$_2$R$_3$  (XI)

in which $R_2$ and $R_3$ have the same meanings as in the formula (I).

This reaction is preferably performed in a chlorinated solvent such as chloroform or methylene chloride, in the presence of a tertiary amine such as triethylamine, at a temperature between 20° C. and the boiling point of the solvent.

The acid chlorides of formula (X) may be obtained by the action of a chlorinating agent such as thionyl chloride on the corresponding acid. This reaction may be carried out in an inert solvent such as chloroform or toluene, preferably at the boiling point of the solvent.

The corresponding acids may be prepared by the hydrolysis of the corresponding ethyl esters. This hydrolysis is generally accomplished by means of aqueous sodium hydroxide solution at the boiling point of the reaction medium.

The ethyl esters may be obtained by the action of a quinolone of formula (II) on ethyl bromoacetate. This reaction is preferably performed in a ketone such as 2-butanone, in the presence of an alkali metal carbonate such as potassium or sodium carbonate, at the boiling point of the solvent.

The compound of formula (I) in which $R_4$ denotes 4-aminophenyl may be obtained by the reduction of 4-{[2-(4-nitrophenyl)-5-trifluoromethyl-4-quinolyl]oxyacetyl}-morpholine.

This reaction is generally accomplished using palladized charcoal and hydrochloric acid, in an alcohol such as methanol, ethanol, isopropanol or a mixture of these solvents.

4-{[2-(4-Nitrophenyl)-5-trifluoromethyl-4-quinolyl]oxyacetyl}morpholine may be obtained by the processes described above for the preparation of the compounds of formula (I).

The reaction mixtures obtained by the various processes described above are treated according to conventional physical methods (evaporation, extraction, distillation, crystallization or chromatography).

The compounds of formula (I) exhibit advantageous pharmacological properties indicative of anxiolytic, hypnotic, anticonvulsant and antiepileptic activity.

These compounds exhibit appreciable affinity in vitro for benzodiazepine receptor sites at concentrations below or equal to 100 nM, according to the technique described by J. C. Blanchard and L. Julou, J. Of Neurochemistry, 40, 601 (1983), based on the work of Squires and Braestrup, Nature, 266, 732 (1977).

In mice, they have proved active at oral doses below or equal to 25 mg/kg with respect to pentetrazole-induced convulsions, according to a technique similar to that of Everett and Richards, J. Pharmacol., 81, 402 (1944).

The compounds of formula (I) exhibit low toxicity. Their LD$_5$O is generally more than 300 mg/kg when administered orally in mice.

The compounds of formula (I) in which $R_1$ denotes trifluoromethyl, $R_2$ and $R_3$ form, together with the nitrogen atom to which they are attached, morpholino, and $R_4$ denotes 4-methylphenyl, 4-chlorophenyl, 4-fluorophenyl, 4-methoxyphenyul, 4-methyl-3-fluorophenyl or 2,4-difluorophenyl are especially advantageous.

EXAMPLES

The examples which follow illustrate the invention, without limiting it.

Example 1

Anhydrous potassium carbonate (2.2 g) is added to a stirred suspension of 2-(4-methylphenyl)-5-trifluoromethyl-4-quinolone (2.4 g) and 4-(2-chloroacetyl)morpholine (1.3 g) in 2-butanone (50 cc). The mixture is heated to reflux for 3 hours and cooled to room temperature (approximately 20° C.). The insoluble matter is removed by filtration and rinsed with 2-butanone. The organic phases are combined and the solvent is removed under reduced pressure. After recrystallation of the residue from acetonitrile, 4-{[2(4-methylphenyl)-5-trifluoromethyl-4-quinolyl]oxyacetyl} morpholine (2.6 g), m.p. 172° C. is isolated.

2-(4-Methylphenyl)-5-trifluoromethyl-4-quinolone may be prepared in the following manner: N-(2acetyl-3-trifluoromethylphenyl)-4-methylbenzamide (2.8 g) and potassium tert-butylate (1.07 g) in toluene (30 cc) are heated to reflux for 1 hour. The mixture is cooled to room temperature (approximately 20° C.), glacial acetic acid (0.55 cc) is added and the mixture is diluted with water (30 cc) and ethyl ether (15 cc). the suspension is stirred for 30 minutes and the precipitate is drained, washed twice with ethyl ether and then with water and finally dried. Its m.p. is above 260° C.

N-(2-Acetyl-3-trifluoromethylphenyl)-4-methylbenzamide may be prepared in the following manner: 2-amino-6-trifluoromethylacetophenone hydrochloride (2.39 g), 4-methylbenzoyl chloride (1.45 cc) and pyridine (1.7 cc) in anhydrous toluene (20 cc) are stirred at room temperature (approximately 20° C.) for 45 minutes. Water (20 cc) and ethyl acetate (80 cc) are then added. The aqueous phase is separated after settling has taken place and the organic phase is washed with water (3×25 cc), dried over magnesium sulphate and evaporated under reduced pressure. The residue obtained is stirred in petroleum ether (50 cc), filtered off and washed with petroleum ether. This operation is repeated twice. N-(2-Acetyl-3-trifluoromethylphenyl)-4-methylbenzamide (2.5 g), m.p. 171° C., is thereby isolated.

2-Amino-6-trifluoromethylacetophenone hydrochloride may be prepared in the following manner: N-(2-acetyl-3-trifluoromethylphenyl)-2,2-dimethylpropionamide (67 g) in a mixture of concentrated hydrochloric acid (670 cc) and ethanol (670 cc) is heated to reflux for 5 hours 30 minutes. The mixture is cooled to room temperature (approximately 20° C.). The solvents are evaporated off under reduced pressure and the crystallized residue is taken up several times with toluene, evaporating on each occasion in order to remove the remaining water, washed with ethyl ether and then with 40°-60° petroleum ether and finally dried under reduced pressure. 2-Amino-6-trifluoromethylacetophenone hydrochloride (50.4 g), m.p. 163° C., is thereby obtained.

N-(2-Acetyl-3-trifluoromethylphenyl)-2,2-dimethylpropionamide may be prepared in the following manner: chromic anhydride (37 g) is added portionwise in the course of 20 minutes to a solution, cooled to −5° C., of N-[2-(α-hydroxyethyl)-3-trifluoromethylphenyl]-2,2-dimethylpropionamide (36 g) in acetone (1000 cc). The mixture is stirred for 15 minutes at −5° C. and a further amount (19 g) f chromic anhydride is then added portion wise,. Stirring is continued for a further 15 minutes at −520 C. and isopropanol (120 cc) is then introduced slowly at this temperature in order to destroy the excess chromic anhydride. The temperature is allowed to rise to room temperature (approximately 20° C.) and the solvent is evaporated off under reduced pressure. The residue is taken up with water (700 cc) and ethyl ether (1000 cc) and is then stirred for one hour. Some slight insoluble matter is removed by filtration and washed with water and ethyl ether. The aqueous and organic phases are combined, and the aqueous phase is separated after settling has taken place and washed with ethyl ether (2×200 cc). The organic phases are combined, washed with water (2×100 cc), 5% strength potassium bicarbonate solution (2×100 cc) and water (2×100 cc), dried over magnesium sulphate and then evaporated under reduced pressure. N-(2-Acetyl-3-trifluoromethylphenyl)-2,2-dimethylpropionamide (34.3 g), m.p. 142° C., is thereby obtained.

N-[2-(α-Hydroxyethyl)-3-trifluoromethylphenyl]-2,2-dimethylpropionamide may be prepared in the following manner: a 1.37 M solution (45 cc) of n-butyllithium in hexane is added in the course of 15 minutes to a solution, placed under a nitrogen atmosphere and cooled to 10° C., of N-(3-trifluoromethylphenyl)-2,2-dimethylpropionamide (7.7 g) in dry tetrahydrofuran (40 cc), and the mixture is stirred for 2 hours at this temperature. The solution is then cooled to −78° C. and acetaldehyde (17.5 cc), cooled to −78° C., is introduced in a single portion. The temperature rises rapidly to 12° C. and then falls again. When the reaction medium is at −10° C., water (150 cc) is added rapidly. After evaporation of the tetrahydrofuran under reduced pressure, the suspension is taken up with ethyl ether (200 cc) and stirred until dissolution has taken place. The aqueous phase is separated after settling has taken place and the organic phase is washed with water (3×20 cc), dried over magnesium sulphate and evaporated under reduced pressure. The residue obtained is taken up with 40°-60° petroleum ether (100 cc) and broken up under reflux. The white suspension thereby obtained is cooled and the precipitate is drained, made into a paste twice with petroleum ether, washed with isopropyl ether previously cooled to −70° C. and finally dried under reduced pressure. N-[2-(α-Hydroxyethyl)-3-trifluoromethylphenyl]-2,2-dimethylpropionamide (6.2 g), m.p. 172° C., is thereby obtained.

N-(3-Trifluoromethylphenyl)-2,2-dimethylpropionamide may be prepared in the following manner: triethylamine (118 cc) is added to a solution, under a nitrogen atmosphere, of 3-trifluoromethylaniline (130 g) in toluene (1300 cc). After the mixture has been cooled to 10° C., pivaloyl chloride (105 cc) is introduced in the course of 45 minutes and the mixture is stirred at a temperature in the region of 20° C. for one hour. The suspension is taken up with water (500 cc) and ethyl acetate (300 cc). The organic phase is separated after settling has taken place and the aqueous phase is washed with ethyl acetate (200 cc). The organic phases are combined, washed with water (300 cc), normal hydrochloric acid solution (200 cc) and then water (200 cc) and dried over magnesium sulphate. The solvent is removed under reduced pressure. The residue obtained is taken up with 40°-60° petroleum ether (3 ×100 cc) and then dried. N-(3-Trifluoromethylphenyl)-2,2-dimethylpropionamide (183.4 g), m.p. 107° C., is thereby obtained.

Example 2

The procedure is as in Example 1, but starting with 2-(4-chlorophenyl)-5-trifluoromethyl-4-quinolone (2.9 g), 4-(2-chloroacetyl)morpholine (1.62 g) and anhydrous potassium carbonate (2.5 g) in 2-butanone (60 cc). After recrystallization in acetonitrile, 4-{[2-(4-chlorophenyl)-5-trifluoromethyl-4-quinolyl]oxyacetyl} morphline (3.2 g), m.p. 179° C., is isolated.

2-(4-Chlorophenyl)-5trifluoromethyl-4-quinolone may be prepared in the following manner; the procedure is as in Example 1 for the preparation of 2-(4-methylphenyl)-5-trifluoromethyl-4-quinolone, starting with N-(2-acetyl-3-trifluoromethylphenyl)-4-chlorobenzamide (3.5 g) and potassium tert-butylate (1.24 g) in toluene (40 cc), the heating times being extended to 1 hour 30 minutes. The m.p. of the product is above 260° C.

N-(2-Acetyl-3-trifluoromethylphenyl)-4-chlorobenzamide may be prepared in the following manner: the procedure is as in Example 1 for the preparation of N-(2-acetyl-3-trifluoromethylphenyl)-4-methylbenzamide, starting with 2-amino-6-trifluoromethylacetophenone hydrochloride (2.7 g), 4-chlorobenzoyl chloride (1.58 cc) and pyridine (2cc) in anhydrous toluene (30 cc), the reaction time being extended to 2 hours. The m.p. of the product is 210° C.

Example 3

The procedure is as in Example 1, but starting with 2-(4-fluorophenyl)-5-trifluoromethyl-4-quinolone (2.6 g), 4-(2-chloroacetyl)morpholine (1.53 g) and anhydrous potassium carbonate (2.35 g) in 2-butanone (60 cc). After recrystallization from an isopropyl ether- /acetonitrile mixture (37:10 by volume), 4-{[2-(4-fluorophenyl)-5-trifluoromethyl-4-quinolyl]oxyacetyl}morpholine (3.2 g), m.p. 154° C., is isolated.

2-(4-Fluorophenyl)-5-trifluoromethyl-4-quinolone may be prepared in the following manner: the procedure is as in Example 1 for the preparation of 2-(4-methylphenyl)-5-trifluoromethyl-4-quinolone, starting with the N-(2-acetyl-3-trifluoromethylphenyl)-4-fluorobenzamide (3 g) and potassium tert-butylate (1.13 g) in toluene (40 cc), the reaction time being extended to 2 hours. The m.p. of the product is above 260° C.

N-(2-Acetyl-3-trifluoromethylphenyl)-4-fluorobenzamide may be prepared in the following manner: the procedure is as in Example 1 for the preparation of N-(2-acetyl-3-trifluoromethylphenyl)-4-methylbenzamide, starting with 2-amino-6-trifluoromethylacetophenone hydrochloride (2.7 g), 4-fluorobenzoyl chloride (1.49 cc) and pyridine (2 cc) in anhydrous toluene (30 cc), the reaction time being extended to 2 hours. The m.p. of the product is 200° C.

Example 4

The procedure is as in Example 1, but starting with 2-(2-fluorophenyl)-5-trifluoromethyl-4-quinolone (2.6 g), 4-(2-chloroacetyl)morpholine (1.53 g) and anhydrous potassium carbonate (2.35 g) in 2-butanone (60 cc), the reaction time being extended to 4 hours 30 minutes. After recrystallization from an isopropyl ether/acetonitrile mixture (37.16 by volume, 4-{[2-(2-fluorophenyl)-5-trifluoromethyl-4-quinolyl]oxyacetyl} morpholine (3.2 g), m.p. 172° C., is isolated.

2-(2-Fluorophenyl)-5-trifluoromethyl-4-quinolone may be prepared in the following manner: the procedure is as in Example 1 for the preparation of 2-(4-methylphenyl)-5-trifluoromethyl-4-quinolone, starting with N-(2-acetyl-3-trifluoromethylphenyl)-2-fluorobenzamide (3.2 g) and potassium tert-butylate (1.2 g) in toluene (40 cc), the reaction time being extended to 2 hours. The m.p. of the product is above 260° C.

N-(2-Acetyl-3-trifluoromethylphenyl)-2-fluorobenzamide may be prepared in the following manner: the procedure is as in Example 1 for the preparation of N-(2-acetyl-3-trifluoromethylphenyl)-4-methylbenzamide, starting with 2-amino-6-trifluoromethylacetophenone hydrochloride (2.7 g), 2-fluorobenzoyl chloride (1.5 cc) and pyridine (2 cc) in anhydrous toluene (30 cc). The m.p of the product is 100° C.

Example 5

The procedure is as in Example 1, but starting with 2-(4-methoxyphenyl)-5-trifluoromethyl-4-quinolone (2.9 g), 4-(2-chloroacetyl) morpholine (1.64 g) and anhydrous potassium carbonate (2.50 g) in 2-butanone (60 cc). After recrystallization from acetonitrile, 4-{[2-(4-methoxyphenyl)-5-trifluoromethyl-4-quinolyl]oxyacetyl}morpholine (3.2 g), m.p. 175° C., is isolated.

2-(4-Methoxyphenyl)-5-trifluoromethyl-4-quinolone may be prepared in the following manner: the procedure is as in Example 1 for the preparation of 2-(4-methylphenyl)-5-trifluoromethyl-4-quinolone, starting with N-(2-acetyl-3-trifluoromethylphenyl)-4-methoxybenzamide (3,34 g) and potassium tert-butylate (1.22 g) in toluene (40 cc), the reaction time being extended to 6 hours. The m.p. of the product is above 260° C.

N-(2-Acetyl-3-trifluoromethylphenyl)-4-methoxybenzamide may be prepared in the following manner: the procedure is as in Example 1 for the preparation of N-(2-acetyl-3-trifluoromethylphenyl)-4-methylbenzamide, starting with 2-amino-6-trifluoromethylacetophenone hydrochloride (2.7 g), 4-methoxybenzoyl chloride (1.75 cc) and pyridine (2 cc) in anhydrous toluene (30 cc), the reaction time being extended to 2 hours. The m.p. of the product is 171° C.

Example 6

The procedure is as in Example 1, but starting with 2-(4-methyl-3-fluorophenyl)-5trifluoromethyl-4-quinolone (2.6 g), 4-(2-chloroacetyl)morpholine (1.46 g) and anhydrous potassium carbonate (2.2 g) in 2-butanone (60 cc). After recrystallization from an isopropyl ether/acetonitrile mixture (34:9 by volume, 4-{[2-(4-methyl-3-fluorophenyl)-5-trifluoromethyl-4-quinolyl]oxyacetyl}morpholine (2.7 g), m.p. 169° C., is isolated.

2-(4-Methyl-3-fluorophenyl)-5-trifluoromethyl-4-quinolone may be prepared in the following manner: the procedure is as in Example 1 for the preparation of 2-(4-methylphenyl)-5-trifluoromethyl-4-quinolone, starting with N-(2-acetyl-3-trifluoromethylphenyl)-4-methyl-3-fluorobenzamide (2.9 g) and potassium tert-butylate (1.06 g) in toluene (40 cc). the m.p. of the product is above 260° C.

N-(2-acetyl-3-trifluoromethylphenyl)-4-methyl-3-fluorobenzamide may be prepared in the following manner: the procedure is as in Example 1 for the preparation of N-(2-acetyl-3-trifluoromethylphenyl)-4-methylbenzamide, starting with 2-amino-6-trifluoromethylacetophenone hydrochloride (2.7 g), 4-methyl-3-fluorobenzoyl chloride (2.32 g) and pyridine (2 cc) in anhydrous toluene (30 cc). The m.p. of the product is 164° C.

Example 7

The procedure is as in Example 1, but starting with 2-(3-fluorophenyl)-5-trifluoromethyl-4-quinolone (1.8 g), 4-(2-chloroacetyl)morpholine (1.06 g) and anhydrous potassium carbonate (1.60 g) in 2-butanone (36 cc). The residue (2.35 g) is dissolved while hot in ethyl acetate (25 cc) and the solution is filtered while hot. 40°-60° Petroleum ether (25cc) is added and the solid which precipitates is separated by filtration and dried. 4-{[2-3-Fluorophenyl)-5-trifluoromethyl-4-quinolyl]oxyacetyl}morpholine (1.77 g), m.p. 157° C., is isolated.

2-(3-Fluorophenyl)-5-trifluoromethyl-4-quinolone may be prepared in the following manner: the procedure is as in Example 1 for the preparation of 2-(4-methylphenyl-5-trifluoromethyl-4-quinolone, starting with N-(2-acetyl-3-trifluoromethylphenyl)-3-fluorobenzamide (2.56 g) and potassium tert-butylate (0.97 g) in toluene (26 cc), the reaction time being extended to 2 hours 30 minutes. The m.p. of the product is above 260° C.

N-(2-Acetyl-3-trifluoromethylphenyl)-3-fluorobenzamide may be prepared in the following manner: the procedure is as in Example 1 for the preparation of N-(2-acetyl- 3-trifluoromethylphenyl)-4-methylbenzamide, starting with 2-amino-6-trifluoromethylacetophenone hydrochloride (2.3 g), 3-fluorobenzoyl chloride (1.68 g) and pyridine (1.7 cc) in anhydrous toluene (26 cc), the reaction time being extended to 2 hours. The m.p. of the produce is 150° c.

Example 8

4-(2-Bromoacetyl)morpholine (7.9 g) in 2-butanone (50 cc) is added to a stirred suspension of a mixture (10 g) of 5-chloro-2-(4-methylphenyl)-4-quinolone and 7-chloro-2-(4-methylphenyl)-4-quinolone and anhydrous potassium carbonate (10.2 g) in 2-butanone (250 cc). The mixture is heated to reflux for 15 hours and cooled to room temperature (approximately 20° C.), the insoluble matter is removed by filtration and the 2-butanone is evaporated off under reduced pressure. The residue is taken up with water (200 cc) and the aqueous phase is extracted with methylene chloride (3×100 cc). The organic phase is separated after settling has taken place, dried and evaporated under reduced pressure. After the residue has been chromatographed twice on silica gel, the first time using a chloroform/ethyl acetate mixture (70:30 by volume) and the second time using a chloroform/ethyl acetate mixture (80:20 by volume) as eluant, the solid obtained is recrystallized in ethyl acetate. 4-{[5-chloro-2-(4-methylphenyl)-4-quinolyl]oxyacetyl}morpholine (2 g), m.p. 170 ° is thereby obtained.

The mixture of 5-chloro-2-(4-methylphenyl)-4-quinolone and 7-chloro-2-(4-methylphenyl)-4-quinolone may be obtained in the following manner: 3-chloroaniline (13 g) and ethyl 4-methylbenzoylacetate (41.2 g) in polyphosphoric acid (40 g) are heated to 150° C. for 20 minutes with stirring. The mixture is then cooled to 90° C. and concentrated hydrochloric acid (10 cc) is added, followed by water (100 cc). The precipitate is drained and washed with water (3×100 cc), ethyl ether (2×50 cc) and acetone (2×50 cc). A mixture (30 g) of 5-chloro-2-(4-methylphenyl)-4-quinolone an d7-chloro-2-(4-methylphenyl)quinolone, which is used without further purification in the subsequent syntheses, is thereby obtained.

Example 9 anhydrous potassium carbonate (2.28 g) is added to a stirred suspension of 2-(4-methylphenyl)-5-methoxy-4-quinolone (2.19 g) and 4-(2-chloroacetyl)morpholine (1.62 g) in 2-butanone (76 cc). The mixture is heated to reflux for 4 hours 20 minutes and cooled to room temperature (approximately 20° C.) and the solvent is evaporated off under reduced pressure. The residue is taken up with water and ethyl acetate and the organic phase is separated after settling has taken place, dried over magnesium sulphate and evaporated under reduced pressure. The residue obtained is chromatographed on silica gel, using a chloroform/acetone mixture (95:5 by volume). The solid collected is stirred in 40°-60° petroleum ether (50 cc). 4-{[2-(4-Methylphenyl)-5-methoxy-4-quinolyl]oxyacetyl}morpholine (2.3 g), m.p. 132° C., is thereby isolated.

2-(4-Methylphenyl)-5-methoxy-4-quinolone may be prepared in the following manner: N-(2-acetyl-3-methoxyphenyl)-4-methylbenzamide (2.27 g) and potassium tert-butylate (1.36 g) in toluene (23 cc) are heated to reflux for 1 hours. The mixture is cooled to room temperature (approximately 20° C.), glacial acetic acid (1.5 cc) is added and the mixture is diluted with water (25 cc). The suspension is stirred for 15 minutes and the precipitate is drained, washed with water, with toluene and with 40°-60° petroleum ether and then dried. The m.p. of the product is 207° C.

N-(2-Acetyl-3-methoxyphenyl)-4-methylbenzamide may be prepared in the following manner: 2-amino-6-methoxyacetophenone (4g), 4-methylbenzoyl chloride (3.5 cc) and pyridine (2.15 cc) in anhydrous toluene (40 cc) are stirred at room temperature (approximately 20° C.) for 1 hour 20 minutes. Water (40 cc) and toluene (60 cc) are then added. The aqueous phase is separated after settling has taken place; the organic phase is washed with water (3×25 cc), dried over magnesium sulphate and evaporated under reduced pressure. The residue obtained is stirred in 40°-60° petroleum ether (75 cc) and ethyl acetate (25 cc), filtered and washed with 40°-60° petroleum ether. N-(2-Acetyl-3-methoxyphenyl)-4-methylbenzamide (2.44 g), m.p. about 48° C., is thereby isolated.

2-Amino-6-methoxyacetophenone may be prepared in the following manner: N-(2-acetyl-3-methoxyphenyl)-2,2-dimethylpropionamide (18 g) in a mixture of concentrated hydrochloric acid (90 cc) and ethanol (90 cc) is heated to reflux for 4 hours 40 minutes. The mixture is cooled to room temperature (approximately 20° C.) and ethyl acetate (100 cc) and saturated potassium carbonate solution (250 cc) are added. The aqueous phase is extracted with ethyl acetate and the organic phase is washed with water. The organic phases are combined, dried over magnesium sulphate and evaporated under reduced pressure. The oil obtained is used without further purification in the subsequent syntheses.

N-(2-Acetyl-3-methoxyphenyl)-2,2-dimethylpropionamide may be prepared in the following manner: chromic anhydride (41 g) is added portionwise in the course of 40 minutes to a solution, cooled to 0° C., of N-[2-(α-hydroxyethyl)-3-methoxyphenyl]-2,2-dimethylpropionamide (35 g) in acetone (525 cc). The mixture is stirred for 1 hour 5 minutes at 0° C. and a further amount (21 g) of chromic anhydride is then added portionwise. Stirring is continued for a further 1 hour 45 minutes at 0° C. and isopropanol (160 cc) is then introduced slowly at this temperature in order to destroy the excess chromic anhydride. The temperature is allowed to rise to room temperature (approximately 20° C.) and the solvent is evaporated off under reduced pressure. The residue is taken up with ethyl acetate (500 cc) and stirred at room temperature. The solid is removed by filtration and washed with ethyl acetate (350 cc). The organic phase is concentrated under reduced pressure and the residue is chromatographed on silica gel by means of a methylene chloride/acetone mixture (99:1 by volume). N-(2-Acetyl-3-methoxyphenyl)-2,2-dimethylpropionamide (7.83 g), m.p. below 48° C., is thereby isolated.

N-[2-(α-Hydroxyethyl)-3-methoxyphenyl]-2,2-dimethylpropionamide may be prepared in the following manner: a 1.37 M solution (90.5 cc) of n-butyllithium in hexane is added in the course of 25 minutes to a solution, placed under a nitrogen atmosphere and cooled to 0° C., of N-(3-methoxyphenyl)-2,2dimethylpropionamide (10 g) in dry tetrahydrofuran (150 cc), and the mixture is stirred for 2 hours at this temperature. The solution is then cooled to −78° C. and acetaldehyde (27 cc), cooled to −78° C., is added in a single portion. The temperature rises rapidly to 4° C. and then falls again. When the temperature has fallen again to −10° C., water (57 cc) and ethyl ether (200 cc) are added rapidly. After phase separation by allowing settling to take place, the aqueous phase is extracted with ethyl ether and the organic phases are combined and evaporated. Isopropyl ether (100 cc) is added to the residue obtained, the residue is ground and crystallizes, 40°-60° petroleum ether (100 cc) is then added and the mixture is stirred for 15 minutes. This treatment is repeated with 40°-60° petroleum ether (50 cc) and isopropyl ether (b 50 cc). After filtration and drying, N-[2-(α-hydroxyethyl)-3-methoxyphenyl]-2,2-dimethylpropionamide (9.65 g), m.p. 159° C., is obtained.

N-(3-Methoxyphenyl)-2,2-dimethylpropionamide may be prepared in the following manner: tyridine (79.7 cc) is added to a stirred solution of 3-methoxyaniline (110.7 g) in toluene (1100 cc), followed by the slow addition of pivaloyl chloride (120.5 cc). The mixture is stirred for 1 hour 15 minutes at a temperature in the region of 20° C. and water (500 cc) is then added. The precipitate is drained, washed with water and toluene and dried in an oven at 70° C. under reduced pressure in the presence of sodium hydroxide pellets. N-(3-Methoxyphenyl)-2,2-dimethylpropionamide (137.4 g), m.p. 126° C., is thereby obtained.

Example 10

Thionyl chloride (1.8 cc) is added slowly to a stirred suspension of [2-(4-methylphenyl)-5-trifluoromethyl-4-quinolyl]oxyacetic acid (3 g) in chloroform (90 cc). The mixture is heated to reflux for 3 hours, the solvent and also the thionyl chloride are evaporated off under reduced pressure and the residue is then taken up twice with chloroform, evaporating on each occasion in order to remove the traces of thionyl chloride. The residue obtained is suspended in chloroform (90 cc), the solution is cooled to about 10° C. and triethylamine (2.2 cc) is added. Still at this temperature, a solution of thiomorpholine (0.8 cc) in chloroform (10 cc) is added. The mixture is stirred for 15 hours at room temperature, the solvent is evaporated off under reduced pressure and the residue is taken up with ethyl acetate (100 cc) and water (60 cc). The organic phase is separated after settling has taken place, washed with water (50 cc) and decinormal sodium hydroxide solution (2×20 cc) and finally with water (20 cc) and then dried over magnesium sulphate. After evaporation of the solvents under reduce pressure, a residue (3.3 g) is isolated and chromatographed on silica gel, using a methylene chloride/ethyl acetate mixture (95:5 by volume). The residue obtained is stirred in 40°-60° petroleum ether (30 cc). 4-{[2-(4-Methylphenyl)-5-trifluoromethyl-4-quinolyl]oxyacetyl}thiomorpholine (1.9 g), m.p. 154° C., is thereby obtained.

[2-(4-Methylphenyl)-5-trifluoromethyl-4-quinolyl]oxyacetic acid may be prepared in the following manner: ethyl [2-(4-methylphenyl)-5-trifluoromethyl-4-quinolyl]oxyacetate (28.6 g) and normal sodium hydroxide solution (115 cc) in water (700 cc) are heated to reflux for 10 hours. The mixture is cooled to room temperature, acidified to pH 5 by adding glacial acetic acid (7 cc) and stirred for 1 hour 30 minutes at 10° C. The precipitate is drained, washed with water and dried. [2-(4-Methylphenyl)-5-trifluoromethyl-4-quinolyl]oxyacetic acid (25.6 g) is obtained [Rf=0.22; silica gel slab chromatography; eluant: ethyl acetate].

Ethyl [2-(4-methylphenyl)-5-trifluoromethyl-4-quinolyl]oxyacetate may be prepared in the following manner: 2-(4-methylphenyl)-5trifluoromethyl-4-quinolone (24.5 g), ethyl bromoacetate (9.9 cc) and anhydrous potassium carbonate (23.4 ) in 2-butanone (730 cc) are heated to reflux for 3 hours 30 minutes. The mixture is cooled to room temperature (approximately 20° Ç.) and the insoluble matter is drained on sintered glass and washed several times with ethyl ether. The organic phases are evaporated under reduced pressure and the residue obtained is taken up with 40°-60° petroleum ether (250 cc) and heated to reflux. The suspension is then cooled to 10° C, with rapid stirring for 30 minutes. The precipitate is drained, washed with a little 40°-60° petroleum ether and dried. Ethyl [2-(4-methylphenyl)-5-trifluoromethyl-4-quinolyl]oxyacetate (28.1 g), m.p. 134° C., is thereby obtained.

Example 11

Thionyl chloride (3cc) is added slowly to a stirred suspension of [2-(4-methylphenyl)-5-trifluoromethyl-4-quinolyl]oxyacetic acid (3 g), prepared according to Example 10, in chloroform (100 cc). The mixture is heated to reflux for 3 hours, the solvent and also the thionyl chloride are evaporated off under reduced pressure and the residue is then taken up twice with chloroform, evaporating on each occasion in order to remove the traces of thionyl chloride. The residue obtained is suspended inc chloroform (100 cc), the solution is cooled to about 10° C. and triethylamine (3 cc) is introduced. Still at this temperature, a solution of N-(2-methoxyethyl)-N-methylamine (1.25 g) in chloroform (10 cc) is added. The mixture is stirred for 15 hours at room temperature (approximately 20 ° C.), the solvent is evaporated off under reduced pressure and the residue is taken up with ethyl ether (100 cc) and water (30 cc). The organic phase is separated after settling has taken place, washed with water (30 cc), decinormal sodium hydroxide solution (2×20 cc) and water (2×20 cc) and then dried over magnesium sulphate. After evaporation of the solvents under reduced pressure, a residue (1.9 g) is isolated and chromatographed on silica gel, using a methylene chloride/ethyl acetate mixture (95:5 by volume). The residue obtained is stirred in 40°-60 ° petroleum ether (20 cc). N-Methyl-N-(2-methoxyethyl)-[2-(4-methylphenyl)-5-trifluoromethyl-4-quinolyl]oxyacetamide (1 g), m.p. 116° C., is thereby obtained.

Example 12

The procedure is as in Example 1, but starting with 2-(2,4-difluorophenyl)-5-trifluoromethyl-4-quinolone (2.3 g), 4-(2-chloroacetyl)morpholine (1.35 g) and anhydrous potassium carbonate (2.3 g) in 2-butanone (70 cc), the reaction time being extended to 5 hours. After recrystallization from acetonitrile, 4-{[2-(2,4-difluorophenyl)-5-trifluoromethyl-4-quinolyl]oxyacetyl}morpholine (2.3 g), m.p. 184° C., is isolated.

2-(2,4-Difluorophenyl)-5-trifluoromethyl-4-quinolone may be prepared in the following manner: the procedure is as in Example 1 for the preparation of 2-(4-methylphenyl)-5-trifluoromethyl-4-quinolone, starting with N-(2-acetyl-3-trifluoromethylphenyl)-2,4-difluorobenzamide (3.4 g) and potassium tert-butylate (1.3 g) in toluene (40 cc), the reaction time being extended to 2 hours 30 minutes. The m.p. of the produce is above 260° C.

N-(2-Acetyl-3-trifluoromethylphenyl)-2,4-difluorobenzamide may be prepared in the following manner: the procedure is as in Example 1 for the preparation of N-(2-acetyl-3-trifluoromethylphenyl)-4-methylbenzamide, starting with 2-amino-6-trifluoromethylacetophenone hydrochloride (3 g), prepared according to Example 1, 2,4-difluorobenzoyl chloride (2.29 g) and pyridine (2.2 cc) in anhydrous toluene (35 cc). This compound possesses an Rf equal to 0.61 (silica gel slab chromatography; eluant: cyclohexane/ethyl acetate, 50:50 by volume).

Example 13

4-(2-Bromoacetyl)morpholine (7.3 g) in 2 butanone (50 cc) is added to a stirred suspension of a mixture (11.2 g of 5-fluoro-2-(4-methylphenyl)-4-quinolone and 7-fluoro-2-(4-methylphenyl)-4-quinolone and anhydrous potassium carbonate (11.3 g) in 2-butanone (250 cc).

The mixture is heated to reflux for 15 hours and cooled to room temperature (approximately 20° C.), the insoluble matter is removed by filtration and the 2-butanone is evaporated off under reduced pressure. The residue is taken up with water (200 cc) and the aqueous phase is extracted with methylene chloride (3×100 cc). The organic phase is separated after settling has taken place, dried and evaporated under reduced pressure. After chromatography of the residue on silica gel by means of cyclohexane/ethyl acetate mixture (70:30 by volume) as eluant, the solid obtained is ground in 40°–60° C. petroleum ether (100 cc). 4-≡[5-fluoro-2-(4-methylphenyl-4-quinolyl]oxyacetyl}morpholine (2.4 g), m.p. 142°–4° C., is thereby obtained.

The mixture of 5-fluoro-2-(4methylphenyl)-4-quinolone and 7-fluoro-2(4-methylphenyl)-4quinolone may be obtained in the following manner: 3-fluoroaniline (7.3 g) and ethyl 4-methylbenzoylacetate (26.7 g) in polyphosphoric acid (27 g) are heated to 150° C. for 30 minutes with efficient stirring. The mixture is then cooled to 90° C. and normal hydrochloric acid (60 cc) is added. The precipitate is drained and washed with water (3×60 cc), then with ethyl ether (3×60 cc) and finally acetone (2×50 cc). A mixture (22.9 g) of 5-fluoro-2-(4-methylphenyl)-4quinolone and 7-fluoro-2-(4-methylphenyl)-4-quinolone, which is used without further purification in the next stage, is thereby obtained.

Example 14

4-{[2-(4-Nitrophenyl)-5-trifluoromethyl-4-quinolyl-]oxyacetyl}morpholine (6.6 g) dissolved in methanol (b 132 cc) is hydrogenated for three hours thirty minutes at atmospheric pressure in the presence of an 8N solution (6.6 cc) of gaseous hydrochloric acid in isopropanol and palladium (0.66 g) supported on charcoal (10% palladium). Distilled water (240 cc) is then added, the mixture is stirred for 10 minutes and the catalyst is thereafter filtered off. Normal aqueous sodium hydroxide solution (45 cc) is added an the precipitate is filtered off, washed with distilled water (3×100 cc) and dried under reduced pressure. The precipitate is dissolved while hot in a cyclohexane/ethyl acetate mixture (50:50 by volume). The solution is filtered and the filtrate is concentrated under reduced pressure. The residue is taken up on petroleum ether, filtered off and dried. 4-{[2-(4-Aminophenyl)-5-trifluoromethyl-4-quinolyl-]oxyacetyl}morpholine (3.16 g,), m.p. 174° C., is thereby obtained.

4-{[2-(4-Nitrophenyl)-5-trifluoromethyl-4-quinolyl-]oxyacetyl}morpholine may be prepared in the following manner: the procedure is as in Example 1 for the preparation of 4-{[2-(4-methylphenyl)-5trifluoromethyl-4-quinolyl]oxyacetyl}morpholine, starting with 2-(4-nitrophenyl)-5-trifluoromethyl-4-quinolone (8 g), anhydrous potassium carbonate (6.6 g) and 4-(2-chloroacetyl)morpholine (4.3 g) in 2-butanone (160 cc). After recrystallization in 2-butanone, 4-{[2-(4-nitrophenyl)-5-trifluoromethyl-4-quinolyl]oxyacetyl}morpholine (6.2 g), m.p. 222° C., is obtained.

2-(4-Nitrophenyl)-5-trifluoromethyl-4-quinolone may be prepared in the following manner: the procedure is as in Example 1 for the preparation of 2-(4-methylphenyl)-5-trifluoromethyl-4-quinolone, starting with N-(2-acetyl-3-trifluoromethylphenyl)-4-nitrobenzamide (10.6 g) and potassium tert-butylate (3.7 g) in a mixture of toluene (106 cc) and dimethylforamide (10 cc). 2-(4-Nitrophenyl)-5-trifluoromethyl-4-quinolone (8.15 g), m.p. above 260° C., is obtained.

N-(2-Acetyl-3-trifluoromethylphenyl)-4-nitrobenzamide may be prepared in the following manner: the procedure is as in Example 1 for the preparation of N-(2-acetyl-3-trifluoromethylphenyl)-4-methylbenzamide, starting with 2-amino-6-trifluoromethylacetophenone hydrochloride (10 g) and 4-nitrobenzoyl chloride (10.1 g) in a mixture of toluene (100 cc) and pyridine (8.4 cc). N-(2-Acetyl-3-trifluoromethylphenyl)-4-nitrobenzamide (10.8 g), m.p. 245° C., is thereby obtained.

The present invention also provides pharmaceutical compositions which contain one or more compounds of formula (I), in association with a compatible and pharmaceutically acceptable adjuvant, diluent and/or coating. These compositions may be employed orally, rectally, parenterally or percutaneously.

As solid compositions for oral administration, tablets, pills, powders (generally in gelatin capsules) or granules may be used. In these compositions, the active product according to the invention is mixed with one or more inert diluents such as sucrose, lactose, starch, cellulose or silica. The compositions can also include substances other than diluents, .e.g. a lubricant such as magnesium stearate or talc, a coloring, a coating (dragees) or a varnish.

As liquid compositions for oral administration, emulsions of a pharmaceutically acceptable nature, solutions, suspensions, syrups and elixirs containing inert diluents such as water, ethanol, glyceral, vegetable oils or liquid paraffin may be used. These compositions can also include substances other than diluents, e.g. wetting, sweetening, flavouring, thickening or stabilizing products.

The compositions according to the invention for parenteral administration can be suspensions, emulsions or sterile aqueous or non-aqueous solutions. As a solvent or vehicle, it is possible to employ propylene glycol, a polyethylene glycol, vegetable oils, especially olive oil, and injectable organic esters, e.g. ethyl oleate. These compositions can also contain adjuvants, especially wetting, tonicity-regulating, emulsifying, stabilizing and dispersant agents. The sterilization can be carried out in several ways, for example using a bacteriological filter, by incorporating sterilizing agents in the composition, by irradiation or by heating. They can also be prepared in the form of sterile solid compositions which can be dissolved at the time of use in sterile water or any other sterile injectable medium.

The compositions for rectal administration are suppositories or rectal capsules which can contain, apart from the active product, excipients such as cocoa butter, suppo-cire, semi-synthetic glycerides or polyethylene glycols.

The compositions for percutaneous administration are creams, ointments, lotions and liniments, in which the active product is combined with liquid or pasty excipients, preferably in combination with a vehicle promoting percutaneous migration.

The medicinal products and compositions according to the invention are especially useful in human therapy in respect of their anxiolytic, hypnotic, anticonvulsant and antiepileptic action.

In human therapy, the doses depend on the effect sought and the period of treatment; they are generally between 10 and 500 mg per day for an adult when administered orally, with unit doses ranging from 2 to 100 mg of active substance. Generally speaking, the doctor will determine the appropriate dosage in accordance with the age, weight and all other factors specific to the patient to be treated.

The examples which follow illustrate compositions according to the invention:

Example A

Gelatin capsules containing 50 mg of active product and having the following composition are prepared according to the usual procedure:

| | |
|---|---|
| 4-{[2-(4-Methylphenyl)-5-trifluoromethyl-4-quinolyl]oxyacetyl}morpholine | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

Example B

Tablets containing 50 mg of active product and having the following composition are prepared according to the usual procedure:

| | |
|---|---|
| 4-{[2-(4-Fluorophenyl)-5-trifluoromethyl-4-quinolyl]oxyacetyl}morpholine | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerine and titanium oxide (72:3.5:24.5) | q.s. 1 245-mg finished film-coated tablet |

Example C

An injectable solution containing 10 mg of active product and having the following composition is prepared:

| | |
|---|---|
| 4-{[2-(4-Methyl-3-fluorophenyl)-5-trifluoromethyl-4-quinolyl]oxyacetyl}morpholine | 10 mg |
| Benzoic acid | 80 mg |
| Benzyl alcohol | 0.06 cc |
| Sodium benzoate | 80 mg |
| Ethanol, 95% strength | 0.4 cc |
| Sodium hydroxide | 24 mg |
| Propylene glycol | 1.6 cc |
| Water | q.s. 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of the formula

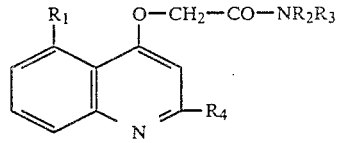

in which $R_1$ is trifluoromethyl; $R_2$ and $R_3$ form, together with the nitrogen atom to which they are attached, morpholino and $R_4$ is 4-methylphenyl, 4-chlorophenyl, 2-,3- or 4-fluorophenyl, 4-methoxyphenyl, 4-methyl-3-fluorophenyl, 2,4-difluorophenyl or 4-aminophenyl;

or $R_2$ or $R_3$ form, together with the nitrogen atom to which they are attached, thiomorpholino and $R_4$ is 4-methylphenyl;

or $R_2$ is methyl, $R_3$ is 2-methoxyethyl and $R_4$ is 4-methylphenyl.

2. A compound according to claim 1 which is 4-{[2-(4-methylphenyl)-5-trifluoromethyl-4-quinolyl]oxyacetyl}morpholine.

3. A compound of the formula

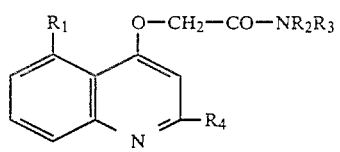

in which $R_1$ is chlorine, fluorine or methoxy; $R_2$ and $R_3$ form, together with the nitrogen atom to which they are attached, morpholino; and $R_4$ is 4-methylphenyl.

4. A pharmaceutical composition useful as an anxiolytic, hypnotic, anticonvulsant or antiepileptic which comprises an anxiolytically-, hypnotically-, anticonvulsantly- or antiepileptically-effective amount of a compound as claimed in claim 1 with a compatible and pharmaceutically acceptable adjuvant, diluent and/or coating.

5. A method of dispelling anxiety, inducing sleep, preventing or relieving convulsions, or combatting epilepsy in a patient which comprises administering to said patient an anxiolytically-, hypotically-, anticonvulsantly- or antiepileptically-effective amount of a compound as claimed in claim 1.

6. A pharmaceutical composition useful as an anxiolytic, hypnotic, anticonvulsant or antiepileptic which comprises an anxiolytically-, hypnotically-, anticonvulsantly- or antiepileptically-effective amount of a compound as claimed in claim 3 with a compatible and pharmaceutically acceptable adjuvant, diluent and/or coating.

7. A method of dispelling anxiety, inducing sleep, preventing or relieving convulsions, or combating epilepsy in a patient which comprises administering to said patient an anxiolytically-, hypnotically-, anticonvulsantly- or antiepileptically-effective amount of a compound as claimed in claim 3.

* * * * *